US010922854B2

United States Patent
Li et al.

(10) Patent No.: US 10,922,854 B2
(45) Date of Patent: Feb. 16, 2021

(54) CT IMAGING

(71) Applicant: Neusoft Medical Systems Co., Ltd., Shenyang (CN)

(72) Inventors: Shuangxue Li, Shenyang (CN); Liguo Zhang, Shenyang (CN)

(73) Assignee: Neusoft Medical Systems Co., Ltd., Shenyang (CN)

( * ) Notice: Subject to any disclaimer, the term of this patent is extended or adjusted under 35 U.S.C. 154(b) by 108 days.

(21) Appl. No.: 16/168,448

(22) Filed: Oct. 23, 2018

(65) Prior Publication Data
US 2019/0122400 A1  Apr. 25, 2019

(30) Foreign Application Priority Data
Oct. 25, 2017  (CN) .......................... 2017 1 1010723

(51) Int. Cl.
*G06T 11/00* (2006.01)
*A61B 6/00* (2006.01)
(Continued)

(52) U.S. Cl.
CPC ............ *G06T 11/008* (2013.01); *A61B 6/032* (2013.01); *A61B 6/488* (2013.01); *A61B 6/5205* (2013.01);
(Continued)

(58) Field of Classification Search
CPC ....... A61B 6/032; A61B 6/488; A61B 6/5205; A61B 6/545; A61B 6/563; A61B 6/566;
(Continued)

(56) References Cited

U.S. PATENT DOCUMENTS 7,042,974 B2 * 5/2006 Goodgame ........... G06T 11/006
378/4
8,517,608 B1 * 8/2013 Arnold ................. A61B 6/5211
378/207
(Continued)

FOREIGN PATENT DOCUMENTS

| CN | 1813635 A | 8/2006 |
|---|---|---|
| CN | 101138506 | 3/2008 |

(Continued)

OTHER PUBLICATIONS

State Intellectual Property Office of the People's Republic of China, Office Action and Search Report Issued in Application No. 201711010723X, dated Mar. 26, 2020, 20 pages, (Submitted with Machine Translation).

(Continued)

*Primary Examiner* — Dominic E Rego
(74) *Attorney, Agent, or Firm* — Fish & Richardson P.C.

(57) ABSTRACT

Methods, devices and apparatus for CT imaging in a CT system are provided. The CT system includes a CT console, a CT scanner and an image reconstruction computer. In one aspect, a method includes detecting, by the CT console, whether a parameter adjustment instruction is received from a user during a scanning process in which a preview image is generated and displayed to the user. If the parameter adjustment instruction is received, the CT console sends adjusted scan parameters to at least one of the CT scanner or the image reconstruction computer such that the CT scanner and the image reconstruction computer generate a new preview image based on the adjusted scan parameters that are determined according to the preview image. If the parameter adjustment instruction is not received, the CT console displays to the user a CT image generated by the (Continued)

image reconstruction computer after finishing the scanning process.

20 Claims, 2 Drawing Sheets

(51) Int. Cl.
 *A61B 6/03* (2006.01)
 *G06T 7/00* (2017.01)
(52) U.S. Cl.
 CPC .............. *A61B 6/542* (2013.01); *A61B 6/545* (2013.01); *G06T 7/0012* (2013.01); *G06T 11/005* (2013.01); *A61B 6/563* (2013.01); *A61B 6/566* (2013.01); *G06T 2211/40* (2013.01)
(58) Field of Classification Search
 CPC ..... A61B 6/542; G06T 11/008; G06T 7/0012; G06T 11/005; G06T 2211/40
 See application file for complete search history.

(56) References Cited

U.S. PATENT DOCUMENTS

| | | | | |
|---|---|---|---|---|
| 9,449,404 | B2* | 9/2016 | Brown | G06T 11/006 |
| 9,959,640 | B2* | 5/2018 | Koehler | G06T 11/60 |
| 2005/0069083 | A1 | 3/2005 | Klingenbeck-Regn | |
| 2005/0270601 | A1* | 12/2005 | Rodrigues | H04N 1/00482 358/527 |
| 2007/0263008 | A1* | 11/2007 | Li | D03C 19/005 345/582 |
| 2007/0286332 | A1* | 12/2007 | Gohno | A61B 6/488 378/15 |
| 2016/0328855 | A1* | 11/2016 | Lay | G06K 9/4614 |
| 2017/0146211 | A1* | 5/2017 | Wu | F21S 45/48 |
| 2017/0188984 | A1* | 7/2017 | Lou | A61B 6/4035 |
| 2018/0014016 | A1* | 1/2018 | Basu | H04N 19/126 |
| 2018/0271511 | A1* | 9/2018 | Stanton | A61B 34/20 |

FOREIGN PATENT DOCUMENTS

| | | |
|---|---|---|
| CN | 101308102 | 11/2008 |
| CN | 101382505 | 3/2009 |
| CN | 103505232 A | 1/2014 |
| CN | 103565457 A | 2/2014 |
| CN | 104125841 A | 10/2014 |
| CN | 104605881 A | 5/2015 |
| CN | 106775530 | 5/2017 |
| DE | 102006021629 A1 | 10/2007 |
| DE | 102010009105 A1 | 8/2011 |
| JP | 09294739 | 11/1997 |

OTHER PUBLICATIONS

State Intellectual Property Office of the People's Republic of China, Office Action and Search Report Issued in Application No. 201711010723.X, dated Nov. 17, 2020, 16 pages (with English Translation).

* cited by examiner

CT IMAGING

CROSS REFERENCE TO RELATED APPLICATIONS

This application claims priority to Chinese Patent Application No. 201711010723.X filed on Oct. 25, 2017, the entire content of which is incorporated herein by reference.

BACKGROUND

CT (Computed Tomography) imaging is one of the major imaging methods in modern medical imaging. A basic principle of the CT imaging is that a subject is scanned with a highly sensitive detector depending on differences of X-ray absorption and transmittance among different tissues of the subject to obtain raw data. Then the raw data is input into a computer. After the computer processes the raw data, a CT image for the subject can be obtained.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices, and systems for computed tomography (CT) imaging, particularly by generating preview images during a scanning process.

One aspect of the present disclosure features a method of CT imaging in a CT system that includes a CT console, a CT scanner, and an image reconstruction computer. The method includes: detecting, by the CT console, that a parameter adjustment instruction is received from a user during a scanning process in which a preview image is generated based on scan parameters and displayed to the user; sending, by the CT console, adjusted scan parameters to at least one of the CT scanner or the image reconstruction computer, where the adjusted scan parameters are determined according to the preview image; and controlling, by the CT console, the CT scanner and the image reconstruction computer to generate a new preview image based on the adjusted scan parameters.

The scan parameters can include exposure parameters and reconstruction parameters. The CT scanner can be configured to obtain raw data by performing an exposure operation based on the exposure parameters during the scanning process when the scanning process has not been completed, and the image reconstruction computer can be configured to generate the preview image by performing an image reconstruction based on the reconstruction parameters and the raw data obtained by the exposure operation.

In some cases, the adjusted scan parameters include adjusted exposure parameters and the reconstruction parameters without adjustment. Sending the adjusted scan parameters to the at least one of the CT scanner or the image reconstruction computer includes: sending the adjusted exposure parameters to the CT scanner, and controlling the CT scanner and the image reconstruction computer to generate a new preview image based on the adjusted scan parameters includes: controlling the CT scanner to stop the exposure operation performed based on the exposure parameters and to perform a new exposure operation based on the adjusted exposure parameters to obtain new raw data; and controlling the image reconstruction computer to perform a new image reconstruction based on the reconstruction parameters and the new raw data to generate the new preview image.

In some cases, the adjusted scan parameters include adjusted reconstruction parameters and the exposure parameters without adjustment. Sending the adjusted scan parameters to the at least one of the CT scanner or the image reconstruction computer includes: sending the adjusted reconstruction parameters to the image reconstruction computer, and controlling the CT scanner and the image reconstruction computer to generate a new preview image based on the adjusted scan parameters includes: controlling the CT scanner to continue the exposure operation based on the exposure parameters without adjustment; and controlling the image reconstruction computer to perform a new image reconstruction based on the adjusted reconstruction parameters and the raw data obtained by the exposure operation to generate the new preview image. The method can further include: notifying, by the CT console, the image reconstruction computer that the exposure parameters are not adjusted, such that the image reconstruction computer retains the raw data obtained by the exposure operation.

In some cases, the adjusted scan parameters include adjusted exposure parameters and adjusted reconstruction parameters. Sending the adjusted scan parameters to at least one of the CT scanner or the image reconstruction computer includes: sending, by the CT console, the adjusted exposure parameters to the CT scanner and the adjusted reconstruction parameters to the image reconstruction computer; controlling the CT scanner to stop the exposure operation based on the exposure parameters and to perform a new exposure operation based on the adjusted exposure parameters to obtain new raw data; and controlling the image reconstruction computer to perform a new image reconstruction based on the adjusted reconstruction parameters and the new raw data to generate the new preview image.

In some implementations, the reconstruction parameters include two or more groups of reconstruction parameters with different values, and the method includes: controlling the image reconstruction computer to perform a respective image reconstruction, based on the raw data obtained by the exposure operation during the scanning process and each of the groups of reconstruction parameters, to generate a respective preview image; and displaying the respective preview images to the user for selection.

The adjusted scan parameters are determined by the user based on the preview image. In some cases, the method includes determining, by the CT console, the adjusted scan parameters based on a result of analyzing the preview image. Analyzing the preview image can include at least one of performing an analysis of artifacts of the preview image, or performing an analysis of noise levels of the preview image.

Another aspect of the present disclosure features a device including: at least one processor; and at least one non-transitory machine-readable storage medium coupled to the at least one processor having machine-executable instructions stored thereon that, when executed by the at least one processor, cause the at least one processor to perform operations including: detecting whether a parameter adjustment instruction is received from a user during a scanning process in which a preview image is generated based on scan parameters and displayed to the user; in response to detecting that the parameter adjustment instruction is received, sending adjusted scan parameters to at least one of a CT scanner or an image reconstruction computer and controlling the CT scanner and the image reconstruction computer to generate a new preview image based on the adjusted scan parameters, where the adjusted scan parameters are determined according to the preview image; and in response to detecting that the parameter adjustment instruction is not received, displaying to the user a CT image generated by the image reconstruction computer after the scanning process has been completed.

The scan parameters can include exposure parameters and reconstruction parameters. The CT scanner can be configured to obtain raw data by performing an exposure operation based on the exposure parameters during the scanning process, and the image reconstruction computer can be configured to generate the preview image by performing an image reconstruction based on the reconstruction parameters and the raw data obtained by the exposure operation.

In some cases, the adjusted scan parameters include adjusted exposure parameters and the reconstruction parameters without adjustment. The operations include: sending the adjusted exposure parameters to the CT scanner; controlling the CT scanner to stop the exposure operation performed based on the exposure parameters and to perform a new exposure operation based on the adjusted exposure parameters to obtain new raw data; and controlling the image reconstruction computer to perform a new image reconstruction based on the reconstruction parameters and the new raw data to generate the new preview image.

In some cases, the adjusted scan parameters include adjusted reconstruction parameters and the exposure parameters without adjustment. The operations include: sending the adjusted reconstruction parameters to the image reconstruction computer; controlling the CT scanner to continue the exposure operation based on the exposure parameters; and controlling the image reconstruction computer to perform a new image reconstruction based on the adjusted reconstruction parameters and the raw data obtained by the exposure operation to generate the new preview image. The operations can further include: notifying the image reconstruction computer that the exposure parameters are not adjusted this time, such that the image reconstruction computer retains the raw data obtained through the exposure operation.

In some cases, the adjusted scan parameters include adjusted exposure parameters and adjusted reconstruction parameters. The operations include: sending the adjusted exposure parameters to the CT scanner and the adjusted reconstruction parameters to the image reconstruction computer; controlling the CT scanner to stop the exposure operation based on the exposure parameters and obtain new raw data by performing a new exposure operation based on the adjusted exposure parameters; and controlling the image reconstruction computer to generate the new preview image by performing a new image reconstruction based on the adjusted reconstruction parameters and the new raw data.

In some implementations, the reconstruction parameters include two or more groups of reconstruction parameters with different values. The operations include: controlling the image reconstruction computer to perform a respective image reconstruction based on the raw data obtained by the exposure operation during the scanning process and each of the groups of reconstruction parameters to generate a respective preview image for selecting by the user.

The adjusted scan parameters can be determined by the user based on the preview image. In some cases, the operations include: determining the adjusted scan parameters based on a result of analyzing the preview image. Analyzing the preview image can include at least one of: performing an analysis of artifacts of the preview image, or performing an analysis of noise levels of the preview image.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
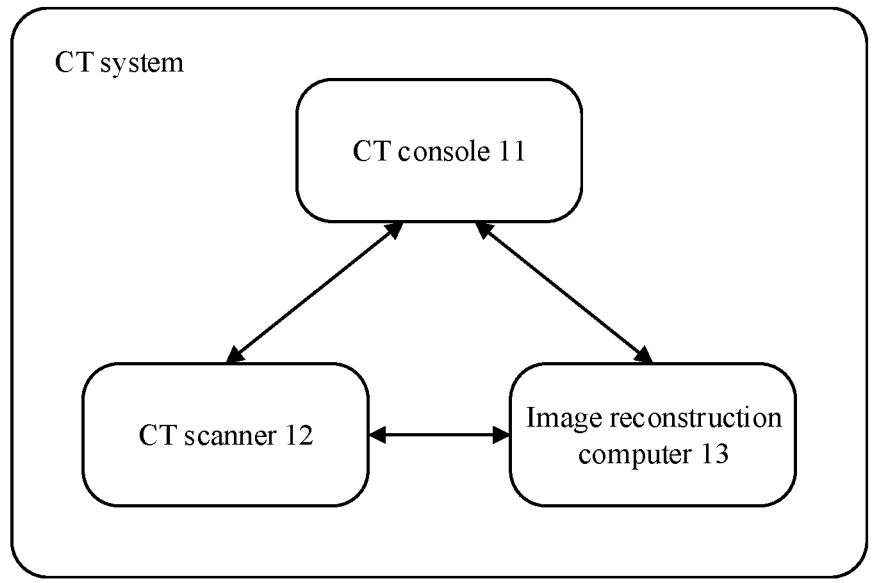
FIG. 1 is a system architecture diagram of an example CT system.

FIG. 1 shows a system architecture diagram of an example CT system. The CT system includes three units: a CT scanner 12, an image reconstruction computer 13, and a CT console 11. A user may control the other units of the CT system through the CT console 11, for example, setting scan parameters, causing the CT scanner 12 to perform a scan process according to the set parameters, and etc. The CT console 11 may send user-set scan parameters to the CT scanner 12 and the image reconstruction computer 13, thereby enabling the CT scanner 12 and the image reconstruction computer 13 to perform a scan process and an image reconstruction based on the user-set scan parameters. The CT scanner 12 can be mainly configured to accomplish a specific scan manner to obtain raw data of a scanned slice for a subject. The image reconstruction computer 13 can be mainly configured to reconstruct a CT image of the subject based on the raw data. The CT console 11 and the image reconstruction computer 13 may be located in a same computer or in different computers, which is not limited in this disclosure. In addition, the CT system may also include an examination bed (not shown) for accurately moving the subject to a predetermined position.

In related arts, the CT console 11 may send user preset scan parameters to the CT scanner 12 and to the image reconstruction computer 13. The CT scanner 12 may perform a scan process based on the preset scan parameters to obtain raw data. The image reconstruction computer 13 may perform an image reconstruction based on the raw data and the preset scan parameters to obtain a CT image available for diagnosis. If an imaging effect of the obtained CT image is not good, for example, the uniformity of CT image, noise levels, slice thickness, or image resolution does not meet diagnostic requirements, a user needs to reset the scan parameters through the CT console 11. The CT console 11 may send the scan parameters reset by the user to the CT scanner 12 and the image reconstruction computer 13 again. The CT scanner 12 may perform a scan process again based on the reset scan parameters to obtain new raw data, and the image reconstruction computer 13 may perform an image reconstruction based on the new raw data to obtain a new CT image.

In practical applications, a CT image with better imaging effect may be obtained by setting scan parameters and performing CT scans multiple times. It takes a long time and resulting in low imaging efficiency. On the other hand, the patient may suffer from excessive radiation dose.

Figure 2:
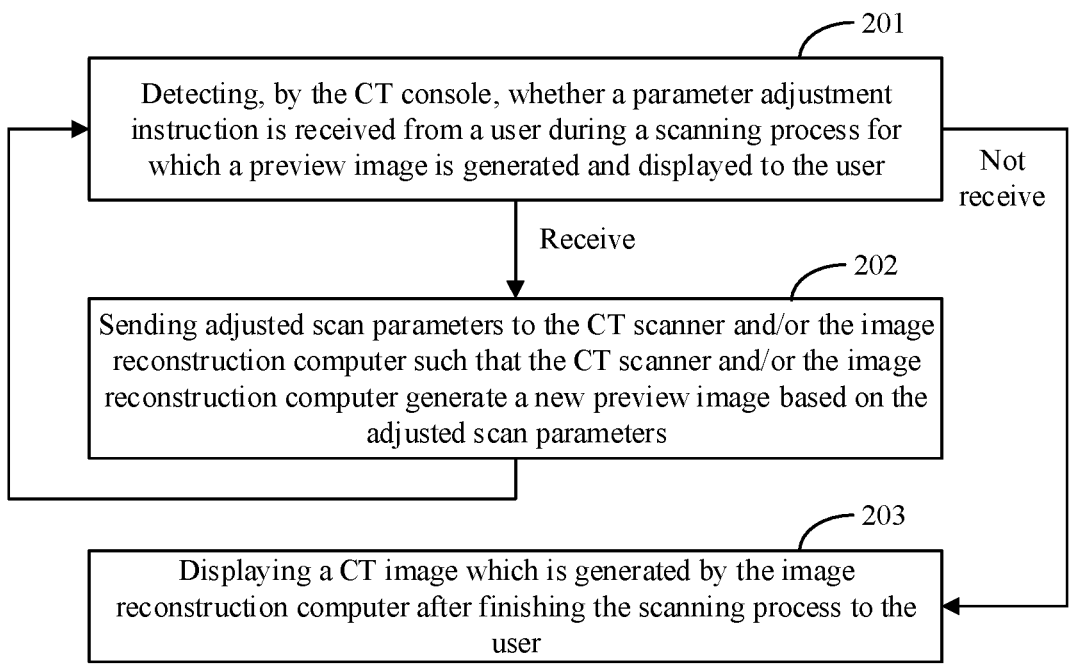
FIG. 2 is a flow chart illustrating a process of a CT imaging method according to an example of the present disclosure.

Implementations of the present disclosure provide CT imaging methods and devices to address the above problems in related arts. Referring to FIG. 2, a flow chart illustrating a process of a CT imaging method according to an example of the present disclosure is shown. The method may be applied to the CT system shown in FIG. 1. As shown in FIG. 1, the CT system includes a CT console 11, a CT scanner 12, and an image reconstruction computer 13. The method may include the following steps.

Step 201: the CT console 11 detects whether a parameter adjustment instruction is received from a user during a scanning process for which a preview image is generated and displayed to the user. When the parameter adjustment instruction is received, step 202 is performed; otherwise step 203 is performed.

Step 202: if the parameter adjustment instruction is received, the CT console 11 may send adjusted scan parameters to the CT scanner 12 and/or the image reconstruction computer 13 such that the CT scanner 12 and/or the image reconstruction computer 13 generate a new preview image based on the adjusted scan parameters, where the adjusted scan parameters are determined according to the preview image obtained at step 201.

Step 203: if the parameter adjustment instruction is not received, the CT console 11 may display a CT image which is generated by the image reconstruction computer 13 after finishing the scanning process to the user.

In the example, the CT console 11 may provide a user interface to the user, and the user may preset scan parameters of the CT system through the user interface. Alternatively, the CT console 11 may provide some default parameter combinations for the user to select. After completing setting of the scan parameters of the CT system, the CT console 11 may send the preset scan parameters to the CT scanner 12 and the image reconstruction computer 13, thereby causing the CT scanner 12 to perform a scanning operation.

It is noted that the image reconstruction computer 13 may generate a preview image during a scanning operation of the CT scanner 12, and send the preview image to the CT console 11. The preview image is displayed to a user by the CT console 11 for viewing. The preview image can be generated by the image reconstruction computer 13 based on at least a portion of raw data obtained by the CT scanner 12 during the scanning process. That is, the preview image generated by the image reconstruction computer 13 during the scanning process is not exactly the same as the CT image generated after the scanning process. For example, the preview image may be reconstructed by the image reconstruction computer 13 with the acquired partial raw data when the scanning process has not been completed. While the CT image is reconstructed by the image reconstruction computer 13 with all raw data after the scanning process is completed. In actual applications, although the preview image is not identical to the CT image, image effects of both images are substantially the same. The image effect may include any of the following: image spatial resolution, image density resolution, image noise, image artifacts, and the like. Thus, by studying the preview image, the user may understand the image effect of the CT image that may eventually be obtained.

Based on the principles described above, during the scanning process performed by the CT scanner 12 based on the scan parameters, the user may view the preview image generated by the image reconstruction computer 13 during the current scanning process at the CT console 11. If the image effect of the preview image does not meet diagnostic requirements, the user may click a parameter adjustment button in the user interface which is provided by the CT console 11. After detecting an operation of the user clicking the parameter adjustment button, the CT console 11 may regard it as receiving a parameter adjustment instruction, and then sends the adjusted scan parameters to the CT scanner 12 and/or the image reconstruction computer 13. After receiving the adjusted scan parameters sent by the CT console 11, the CT scanner 12 may stop the current scan process and perform a new scan process based on the adjusted scan parameters. The adjusted scan parameters may be determined by the user based on the preview image generated during the current scanning process and input via the user interface provided by the CT console 11. Alternately, the CT console 11 may analyze the preview images generated during the current scanning process and may determine the adjusted scan parameters automatically based on analysis results.

During the re-execution of the scan process by the CT scanner 12 based on the adjusted scan parameters, the image reconstruction computer 13 may generate a new preview image in this scan process according to the adjusted scan parameters. Likewise, if the user sees that the image effect of the new preview image at the CT console 11 still does not meet the diagnostic requirements, the parameter adjustment button in the user interface provided by the CT console 11 may be clicked again. After detecting the operation of the user clicking the parameter adjustment button, the CT console 11 may regard as receiving the parameter adjustment instruction, and then sends new adjusted scan parameters to the CT scanner 12 and/or the image reconstruction computer 13. After receiving the new adjusted scan parameters sent by the CT console 11, the CT scanner 12 may stop the current scan process and perform a new scan process based on the new adjusted scan parameters. The new adjusted scan parameters may be determined by the user based on the preview image generated during the current scanning process and input via the user interface provided by the CT console 11. Alternately, the CT console 11 may analyze the preview image generated during the current scanning process and may determine the new adjusted scan parameters automatically based on analysis results.

On the other hand, during the scanning operation by the CT scanner 12 based on the scan parameters, if the user sees that the image effect of the preview image generated during the current scanning process at the CT console 11 meet the diagnostic requirements, a scan parameter adjustment is not required. Thus, the parameter adjustment button in the user interface provided by the CT console 11 is not clicked. In this way, the CT scanner 12 may complete the current scanning operation, and the CT console 11 presents the CT image generated by the image reconstruction computer 13 after completion of the scan to the user for viewing and subsequent diagnosis.

As can be seen by the above example, a preview image is reconstructed based on partial raw data during a scanning operation of the CT scanner 12 by the image reconstruction computer 13, such that a user may issue a parameter adjustment instruction through the CT console 11 immediately when image effect of the preview image is not met diagnostic requirements. Then the CT scanner 12 may immediately stop the scan process, and perform a new scan process based on adjusted scan parameters. In this way, the CT system does not need to perform a new scan process after completing a whole scan process, thereby shortening time for obtaining a CT image available for diagnostic, improving imaging efficiency, and improving subsequent diagnostic efficiency.

In CT imaging, a subject may be irradiated with X-rays, and the subject can be scanned with a highly sensitive detector depending on differences of X-ray absorption and transmittance among different tissues of the subject to acquire raw data. The above step may be referred to as an exposure operation. The step of processing the acquiring raw data by using a computer to obtain a CT image of the subject may be referred to as an image reconstruction. The scanning parameters of the CT system can include exposure parameters (e.g., exposure dose, rotational speed, helical pitch, etc.) and reconstruction parameters (e.g., image resolution, slice thickness, slice interval, reconstruction center, reconstruction matrix, etc.). The CT scanner 12 may perform an exposure operation based on the exposure parameters, and the image reconstruction computer 13 may perform an image reconstruction based on the reconstruction parameters.

At the beginning of a scan, the CT console 11 may send user preset exposure parameters to the CT scanner 12 and preset reconstruction parameters to the image reconstruction computer 13, respectively. The CT scanner 12 may perform an exposure operation based on the preset exposure parameters and send raw data obtained by the exposure operation to the image reconstruction computer 13. The image reconstruction computer 13 may perform an image reconstruction to generate a preview image based on the preset reconstruction parameters and the raw data.

If a user sees that an image effect of the preview image at the CT console 11 does not meet diagnostic requirements, the user may click a parameter adjustment button in a user interface which is provided by the CT console 11 to adjust the exposure parameters and/or the reconstruction parameters. For example, if the user considers that the image effect of the preview image generated by the image reconstruction computer 13 is not effective, except for a case of artifacts, it may be due to insufficient exposure dose, resulting in poor signal to noise ratio and unclear image display. Therefore, the user can adjust the exposure dose in the exposure parameters through the user interface. In another example, an image with small slice thickness has a poor signal to noise ratio, but it may be beneficial to analyze the lesion. An image with a large slice thickness has a better signal to noise ratio, but it may not be helpful to analyze the lesion. Therefore, the user may adjust the slice thickness in the reconstruction parameters according to actual needs in the user interface.

After detecting the operation of the user clicking the parameter adjustment button, the CT console 11 may regard it as receiving a parameter adjustment instruction, and then sends the adjusted exposure parameters to the CT scanner 12 and the adjusted reconstruction parameters to the image reconstruction computer 13 respectively.

Of course, the CT console 11 itself may analyze artifacts and noise levels of the generated preview image after receiving a parameters adjustment instruction, thereby adjusting the exposure parameters and the reconstruction parameters automatically. The CT console 11 may also provide two or more groups of reconstruction parameters with different values to the image reconstruction computer 13, so that the image reconstruction computer 13 may perform image reconstructions based on the raw data obtained by the exposure operation during the scanning process and each of the groups of reconstruction parameters such that different preview images are generated for selecting by the user. The user may study these different preview images at the CT console 11 and select an image most suitable for diagnose. Subsequently, reconstruction parameters used by the selected preview image are determined as the adjusted reconstruction parameters.

In some examples, if the adjusted scan parameters include only adjusted exposure parameters, the CT console 11 only needs to send the adjusted exposure parameters to the CT scanner 12. After receiving the adjusted exposure parameters sent by the CT console 11, the CT scanner 12 may immediately stop current exposure operation based on unadjusted exposure parameters and discard raw data obtained by the current exposure operation. Then the CT scanner 12 executes a new exposure operation based on the adjusted exposure parameters to obtain new raw data. Since reconstruction parameters are not adjusted, the image reconstruction computer 13 may performing a new image reconstruction based on the unadjusted reconstruction parameters and the new raw data sent by the CT scanner 12 to generate a new preview image.

In some examples, if the adjusted scan parameters include only adjusted reconstruction parameters, the CT console 11 only needs to send the adjusted reconstruction parameters to the image reconstruction computer 13 and notify the image reconstruction computer 13 that the exposure parameters are not adjusted at the same time. Since the exposure parameters are not adjusted, the CT scanner 12 may continue to perform the current exposure operation based on unadjusted exposure parameters and retain raw data obtained in the exposure operation previously. Raw data obtained by the continuously exposure operation is sent to the image reconstruction computer 13. When the adjusted reconstruction parameters and information of exposure parameters unadjusted sent by the CT console 11 are received, the image reconstruction computer 13 may stop the current image reconstruction, retain previously received raw data, and continuously receive the raw data sent by the CT scanner 12. A new preview image is generated by performing a new image reconstruction based on the adjusted reconstruction parameters, the previously received raw data, and the continuously received raw data. The received raw data is obtained by the current exposure operation.

In some examples, if the adjusted scan parameters include adjusted exposure parameters and adjusted reconstruction parameters, the CT console 11 may send the adjusted exposure parameters to the CT scanner 12 and send the adjusted reconstruction parameters to the image reconstruction computer 13. After receiving the adjusted exposure parameters sent by the CT console 11, the CT scanner 12 may immediately stop the current exposure operation based on unadjusted exposure parameters and discard raw data obtained by the exposure operation. Then the CT scanner 12 executes a new exposure operation to obtain new raw data, and sends the new raw data related to the new exposure operation to the image reconstruction computer 13. When the adjusted reconstruction parameters sent by the CT console 11 are received, the image reconstruction computer 13 may stop current image reconstruction, and discard previously received raw data. Then a new preview image is generated by performing a new image reconstruction based on the adjusted reconstruction parameters and the new raw data sent by the CT scanner 12.

As described above, in the case that a CT image with a better imaging effect is obtained by setting parameters and performing CT scans multiple times, the CT scanner does not necessarily need to complete multiple exposure operations according to the method provided in the present disclosure. In this way, the number of times a subject is irradiated with X-rays may be effectively reduced, and a radiation dose received by the subject may be lowered.

Corresponding to examples of the CT imaging method described above, the present disclosure also provides an example of a CT imaging device.

Figure 3:
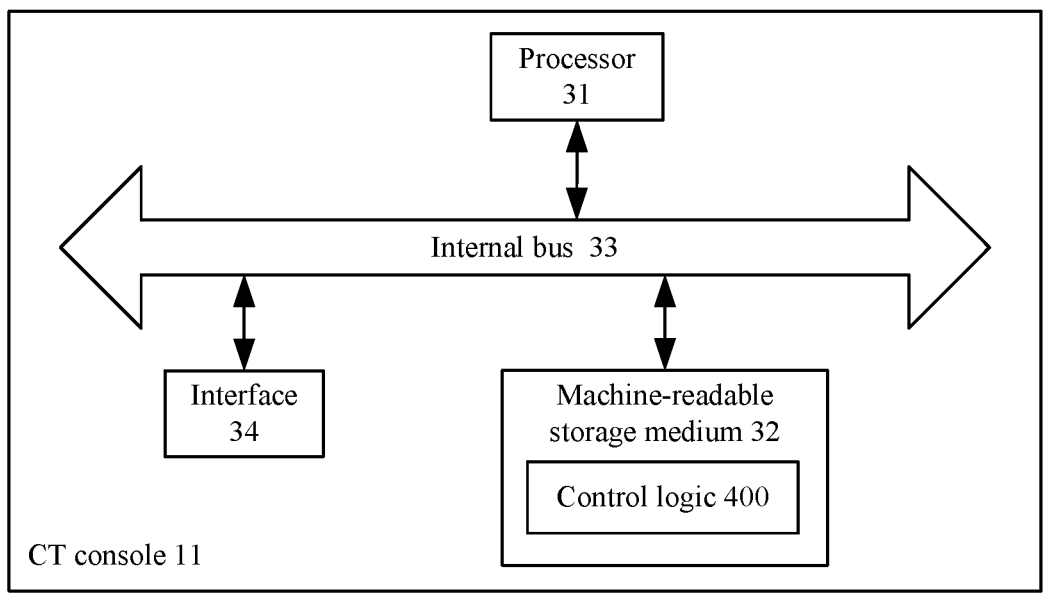
FIG. 3 is a schematic diagram illustrating a hardware structure of a CT imaging device in a CT console according to an example of the present disclosure.

The CT imaging device of the present disclosure may be applied to a CT console. As shown in FIG. 3, a schematic diagram illustrates a hardware structure of a CT imaging device in a CT console according to an example of the present disclosure. In addition to a processor 31, machine-readable storage medium 32, an internal bus 33, and an interface 34 shown in FIG. 3, the CT console where the imaging device is located may also include other hardware according to its actual functions, which is not described in further detail herein. The processor 31, the machine-readable storage medium 32, and the interface 34 may be connected to each other through the internal bus 33. The interface 34 may be configured to provide a user interface with a parameter adjustment button to a user.

In different examples, the machine readable storage medium 32 may be a Radom Access Memory (RAM), a volatile memory, a non-volatile memory, a flash memory, a storage drive (e.g., hard disk drive), a solid state hard disk, any type of storage disk (e.g., compact disk, Digital Video Disk (DVD)), or a similar storage medium, or a combination thereof.

Figure 4:
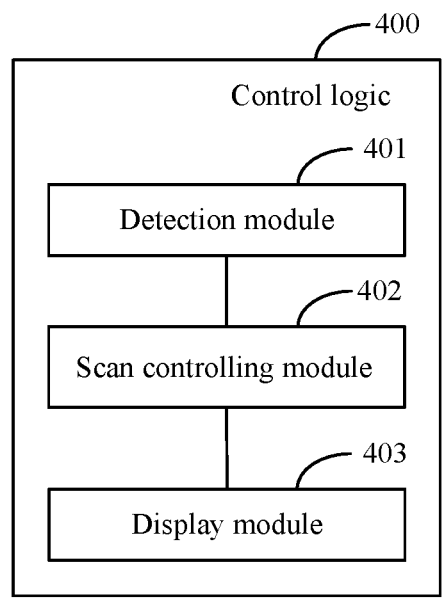
FIG. 4 is a schematic diagram illustrating a functional module of CT imaging control logic according to an example of the present disclosure.

Further, the machine readable storage medium 32 stores control logic 400 for CT imagining. Referring to FIG. 4, a schematic diagram illustrates a functional module of CT imaging control logic according to an example of the present disclosure. The control logic 400 may be applied to the CT imaging device shown in FIG. 3. Functionally, the control logic includes: a detection module 401, a scan controlling module 402, and a display module 403.

The detection module 401 is configured to detect whether a parameter adjustment instruction issued by a user is received after a preview image generated during a scanning process is displayed to the user.

The scan controlling module 402 is configured to control the CT scanner and/or the image reconstruction computer to generate a new preview image based on adjusted scan parameters which are determined according to the preview image and sent to the CT scanner and/or the image reconstruction computer.

The display module 403 is configured to display a CT image or a preview image to the user. The CT image is generated by the image reconstruction computer after the scanning process and the preview image is generated by the image reconstruction computer during the scanning process.

According to the device provided by the present disclosure, the number of times a subject is irradiated with X-rays may be effectively reduced, and a radiation dose received by the subject may be lowered.

A software implementation is taken as an example below to further describe how a CT imaging device executes the control logic 400. In this example, the control logic 400 of the present disclosure should be understood as computer instructions stored in the machine readable storage medium 32. When the processor 31 on the CT imaging device of the present disclosure executes the control logic 400, the processor 31 may perform the following operations by invoking the instructions corresponding to the control logic 400 stored on the machine readable storage medium 32.

Whether a parameter adjustment instruction is received from a user is detected during a scanning process for which a preview image is generated and displayed to the user.

If the parameter adjustment instruction is received, adjusted scan parameters are sent to the CT scanner and/or the image reconstruction computer such that the CT scanner and/or the image reconstruction computer generate a new preview image based on the adjusted scan parameters, where the adjusted scan parameters are determined according to the preview image.

If the parameter adjustment instruction is not received, a CT image which is generated by the image reconstruction computer is displayed after the scanning process to the user.

Further, the scan parameters include exposure parameters and reconstruction parameters.

The CT scanner is configured to obtain raw data by performing an exposure operation based on exposure parameters during the scanning process.

The image reconstruction computer is configured to generate the preview image or the CT image by performing an image reconstruction based on the reconstruction parameters and the raw data obtained by the exposure operation.

Under the condition that the adjusted scan parameters include adjusted exposure parameters, when the processor sends the adjusted scan parameters to the CT scanner and/or the image reconstruction computer such that the CT scanner and/or the image reconstruction computer generate a new preview image based on the adjusted scan parameters, the followings may be specifically included.

The adjusted exposure parameters are sent to the CT scanner.

The CT scanner is controlled to stop the exposure operation based on unadjusted exposure parameters and perform a new exposure operation based on the adjusted exposure parameters to obtain new raw data.

The image reconstruction computer is controlled to perform a new image reconstruction based on unadjusted reconstruction parameters and the new raw data to generate the new preview image.

Under the condition that the adjusted scan parameters only include adjusted reconstruction parameters, when the processor sends the adjusted scan parameters to the CT scanner and/or the image reconstruction computer such that the CT scanner and/or the image reconstruction computer generate a new preview image based on the adjusted scan parameters, the followings may be specifically included.

The adjusted reconstruction parameters are sent to the image reconstruction computer.

The CT scanner is controlled to continue the exposure operation based on unadjusted exposure parameters.

The image reconstruction computer is controlled to perform a new image reconstruction based on the adjusted reconstruction parameters and the raw data obtained by the exposure operation.

Further, under the condition that the adjusted scan parameters only include adjusted reconstruction parameters, when the processor sends the adjusted scan parameters to the CT scanner and/or the image reconstruction computer such that the CT scanner and/or the image reconstruction computer generate a new preview image based on the adjusted scan parameters, the followings may be specifically included.

The image reconstruction computer is notified that the exposure parameters are not adjusted this time, so that the image reconstruction computer retains the raw data obtained through the exposure operation.

Under the condition that the adjusted scan parameters include adjusted exposure parameters and adjusted reconstruction parameters, when the processor sends the adjusted scan parameters to the CT scanner and/or the image reconstruction computer such that the CT scanner and/or the image reconstruction computer generate a new preview image based on the adjusted scan parameters, the followings may be specifically included.

The adjusted exposure parameters are sent to the CT scanner and the adjusted reconstruction parameters are sent to the image reconstruction computer.

The CT scanner is controlled to stop the exposure operation based on unadjusted exposure parameters and obtain new raw data by performing a new exposure operation based on the adjusted exposure parameters.

The image reconstruction computer is controlled to generate the new preview image by performing a new image reconstruction based on the adjusted reconstruction parameters and the new raw data.

Further, the reconstruction parameters include two or more groups of reconstruction parameters with different values.

The image reconstruction computer is performed image reconstructions based on the raw data obtained by the exposure operation during the scanning process and each of the groups of reconstruction parameters such that different preview images are generated for selecting by the user.

Further, the adjusted scan parameters can be determined by the user based on the preview image.

Further, the adjusted scan parameters can be determined based on a result of analyzing the preview image.

Further, when the processor analyzes the preview image, any one or more of the following may be specifically included.

An analysis of artifacts of the preview image can be performed.

An analysis of noise levels of the preview image can be performed.

For the device example, since it basically corresponds to the method examples, it can be referred to the partial description of the method examples. The device examples described above are merely illustrative, where units described as separate components may or may not be physically separated, and the components displayed as units may or may not be physical units, that is, may be located in a place, or they can be distributed to multiple network units. Some or all of the modules may be selected according to actual needs to achieve objectives of the present disclosure. Those of ordinary skill in the art can understand and implement without any creative effort.

The term used in the present disclosure is for the purpose of describing a particular example only, and is not intended to be limiting of the present disclosure. The singular forms such as "a", 'said", and "the" used in the present disclosure and the appended claims are also intended to include multiple, unless the context clearly indicates otherwise. It is also to be understood that the term "and/or" as used herein refers to any or all possible combinations that include one or more associated listed items.

It is to be understood that although different information may be described using the terms such as first, second, third, etc. in the present disclosure, this information should not be limited to these terms. These terms are used only to distinguish the same type of information from each other. For example, the first information may also be referred to as the second information without departing from the scope of the present disclosure, and similarly, the second information may also be referred to as the first information. Depending on the context, the word "if" as used herein may be interpreted as "when" or "as" or "determining in response to".

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

What is claimed is:

1. A method of Computed Tomography (CT) imaging in a CT system that includes a CT console, a CT scanner, and an image reconstruction computer, the method comprising:
    detecting, by the CT console, that a parameter adjustment instruction is received from a user during a scanning process in which a preview image is generated by the image reconstruction computer based on scan parameters and displayed to the user, wherein the preview image is generated based on at least a portion of raw data obtained by the CT scanner when the scanning process has not been completed;
    sending, by the CT console, adjusted scan parameters to at least one of the CT scanner or the image reconstruction computer, wherein the adjusted scan parameters are determined according to the preview image; and
    controlling, by the CT console, the CT scanner and the image reconstruction computer to generate a new preview image based on the adjusted scan parameters when the scanning process is re-executed and has not been completed.

2. The method of claim 1, wherein the scan parameters include exposure parameters and reconstruction parameters,
    wherein the CT scanner is configured to obtain the at least a portion of raw data by performing an exposure operation based on the exposure parameters during the scanning process when the scanning process has not been completed, and
    wherein the image reconstruction computer is configured to generate the preview image by performing an image reconstruction based on the reconstruction parameters and the at least a portion of raw data obtained by the exposure operation.

3. The method of claim 2, wherein the adjusted scan parameters include adjusted exposure parameters and the reconstruction parameters without adjustment,
wherein sending the adjusted scan parameters to the at least one of the CT scanner or the image reconstruction computer comprises: sending the adjusted exposure parameters to the CT scanner, and
wherein controlling the CT scanner and the image reconstruction computer to generate a new preview image based on the adjusted scan parameters comprises:
controlling the CT scanner to stop the exposure operation performed based on the exposure parameters and to perform a new exposure operation based on the adjusted exposure parameters to obtain new raw data; and
controlling the image reconstruction computer to perform a new image reconstruction based on the reconstruction parameters and the new raw data to generate the new preview image.

4. The method of claim 2, wherein the adjusted scan parameters include adjusted reconstruction parameters and the exposure parameters without adjustment,
wherein sending the adjusted scan parameters to the at least one of the CT scanner or the image reconstruction computer comprises: sending the adjusted reconstruction parameters to the image reconstruction computer, and
wherein controlling the CT scanner and the image reconstruction computer to generate a new preview image based on the adjusted scan parameters comprises:
controlling the CT scanner to continue the exposure operation based on the exposure parameters without adjustment; and
controlling the image reconstruction computer to perform a new image reconstruction based on the adjusted reconstruction parameters and the raw data obtained by the exposure operation to generate the new preview image.

5. The method of claim 4, further comprising:
notifying, by the CT console, the image reconstruction computer that the exposure parameters are not adjusted, such that the image reconstruction computer retains the raw data obtained by the exposure operation.

6. The method of claim 2, wherein the adjusted scan parameters include adjusted exposure parameters and adjusted reconstruction parameters,
wherein sending the adjusted scan parameters to at least one of the CT scanner or the image reconstruction computer comprises:
sending, by the CT console, the adjusted exposure parameters to the CT scanner and the adjusted reconstruction parameters to the image reconstruction computer;
controlling the CT scanner to stop the exposure operation based on the exposure parameters and to perform a new exposure operation based on the adjusted exposure parameters to obtain new raw data; and
controlling the image reconstruction computer to perform a new image reconstruction based on the adjusted reconstruction parameters and the new raw data to generate the new preview image.

7. The method of claim 2, wherein the reconstruction parameters comprise two or more groups of reconstruction parameters with different values, and wherein the method comprises:
controlling the image reconstruction computer to perform a respective image reconstruction, based on the raw data obtained by the exposure operation during the scanning process and each of the groups of reconstruction parameters, to generate a respective preview image; and
displaying the respective preview images to the user for selection.

8. The method of claim 1, wherein the adjusted scan parameters are determined by the user based on the preview image.

9. The method of claim 1, further comprising:
determining, by the CT console, the adjusted scan parameters based on a result of analyzing the preview image.

10. The method of claim 9, wherein analyzing the preview image comprises at least one of
performing an analysis of artifacts of the preview image, or
performing an analysis of noise levels of the preview image.

11. A device comprising:
at least one processor; and
at least one non-transitory machine-readable storage medium coupled to the at least one processor having machine-executable instructions stored thereon that, when executed by the at least one processor, cause the at least one processor to perform operations comprising:
detecting whether a parameter adjustment instruction is received from a user during a scanning process in which a preview image is generated by an image reconstruction computer based on scan parameters and displayed to the user, wherein the preview image is generated based on at least a portion of raw data obtained by a Computed Tomography (CT) scanner when the scanning process has not been completed;
in response to detecting that the parameter adjustment instruction is received, sending adjusted scan parameters to at least one of the CT scanner or the image reconstruction computer and controlling the CT scanner and the image reconstruction computer to generate a new preview image based on the adjusted scan parameters when the scanning process is re-executed and has not been completed, wherein the adjusted scan parameters are determined according to the preview image; and
in response to detecting that the parameter adjustment instruction is not received, displaying to the user a CT image generated by the image reconstruction computer after the scanning process has been completed.

12. The device of claim 11, wherein the scan parameters include exposure parameters and reconstruction parameters,
wherein the CT scanner is configured to obtain the at least a portion of raw data by performing an exposure operation based on the exposure parameters during the scanning process, and
wherein the image reconstruction computer is configured to generate the preview image by performing an image reconstruction based on the reconstruction parameters and the at least a portion of raw data obtained by the exposure operation.

13. The device of claim 12, wherein the adjusted scan parameters include adjusted exposure parameters and the reconstruction parameters without adjustment, and
wherein the operations comprise:

sending the adjusted exposure parameters to the CT scanner;

controlling the CT scanner to stop the exposure operation performed based on the exposure parameters and to perform a new exposure operation based on the adjusted exposure parameters to obtain new raw data; and controlling the image reconstruction computer to perform a new image reconstruction based on the reconstruction parameters and the new raw data to generate the new preview image.

14. The device of claim 12, wherein the adjusted scan parameters include adjusted reconstruction parameters and the exposure parameters without adjustment, and wherein the operations comprise:

sending the adjusted reconstruction parameters to the image reconstruction computer;

controlling the CT scanner to continue the exposure operation based on the exposure parameters; and controlling the image reconstruction computer to perform a new image reconstruction based on the adjusted reconstruction parameters and the raw data obtained by the exposure operation to generate the new preview image.

15. The device of claim 14, wherein the operations further comprise:

notifying the image reconstruction computer that the exposure parameters are not adjusted this time, such that the image reconstruction computer retains the raw data obtained through the exposure operation.

16. The device of claim 12, wherein the adjusted scan parameters include adjusted exposure parameters and adjusted reconstruction parameters, and wherein the operations comprise:

sending the adjusted exposure parameters to the CT scanner and the adjusted reconstruction parameters to the image reconstruction computer;

controlling the CT scanner to stop the exposure operation based on the exposure parameters and obtain new raw data by performing a new exposure operation based on the adjusted exposure parameters; and controlling the image reconstruction computer to generate the new preview image by performing a new image reconstruction based on the adjusted reconstruction parameters and the new raw data.

17. The device of claim 12, wherein the reconstruction parameters comprise two or more groups of reconstruction parameters with different values, and wherein the operations comprise:

controlling the image reconstruction computer to perform a respective image reconstruction based on the raw data obtained by the exposure operation during the scanning process and each of the groups of reconstruction parameters to generate a respective preview image for selecting by the user.

18. The device of claim 11, wherein the adjusted scan parameters are determined by the user based on the preview image.

19. The device of claim 11, wherein the operations comprise:

determining the adjusted scan parameters based on a result of analyzing the preview image.

20. The device of claim 19, wherein analyzing the preview image comprises at least one of:

performing an analysis of artifacts of the preview image, or performing an analysis of noise levels of the preview image.

* * * * *